Figure 1:
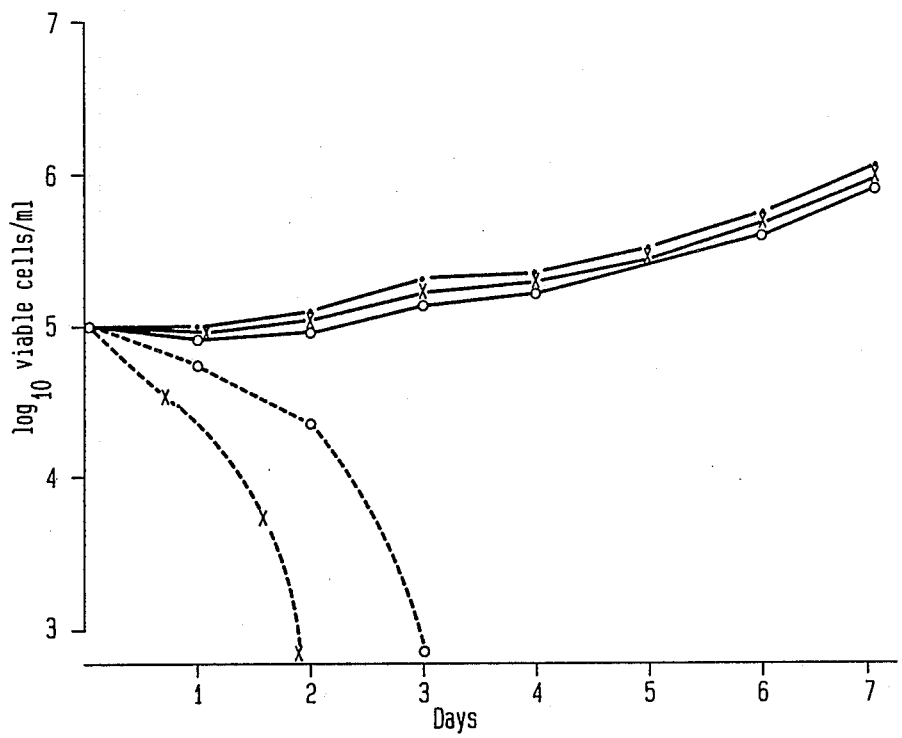

United States Patent [19]

Sutton et al.

[11] Patent Number: 4,957,910

[45] Date of Patent: Sep. 18, 1990

[54] METHOD AND COMPOSITION FOR THE TREATMENT AND PREVENTION OF VIRAL INFECTIONS

[75] Inventors: Peter M. Sutton, Manderley; Anthony Atkinson, Twingley; Graham Lloyd, East Gomeldon, all of England

[73] Assignee: Public Health Laboratory Service Board, London, England

[21] Appl. No.: 165,300

[22] Filed: Mar. 8, 1988

[30] Foreign Application Priority Data

Mar. 17, 1987 [GB] United Kingdom ................. 8706313

[51] Int. Cl.$^5$ ............................................. A61K 31/56
[52] U.S. Cl. ..................................... 514/182; 514/934
[58] Field of Search ........................................ 514/182

[56] References Cited

U.S. PATENT DOCUMENTS 4,100,276 11/1978 Von Daehne et al. ......... 514/182 X
4,681,876  7/1987 Marples et al. ...................... 514/182

OTHER PUBLICATIONS

Reimund, E. Envelope perturbation and AIDS, Lancet 1986; 2:1159.
Chemical Abstracts 93:210277s, (1980).
Brugh, M. Butylated hydroxytoluene protects chickens exposed to Newcast disease virus. Science 1977; 197:1291–92.
Neale, G., Lewis, B., Weaver, V., Panveliwalla, D. Serum bile acids in liver disease. Gut 1971; 12:145–152.
Cowen, A. E., Korman, M. G., Hoffmann, A. F., Thomas, P. J. Plasma disappearance of radioactivity after travenous injection of labelled bile acids in man. Gastroenterology 1975; 68:1567–1573.
Laemmli, U. K. Cleavage of structural proteins during the assembly of the head of bacteriophage T4. Nature, London 1970;227:680–685.
Towbin, H., Staehelin, T. and Gordon, J. Electrophoretic transfer of proteins from polyacrylamidde gels to nitrocellulose sheets: procedure and some applications. Proc. Nat. Acad. Sci., U.S. 1979; 76:4350–4354.
Dunn, S. D. Effects of modification of transfer buffer composition and the renaturation of proteins in gels on the recognition of proteins on Western blots by monoclonal antibodies. Analyt. Biochem. 1986; 157:144–153.
Gallo, R. C., Gallagher, R. E. and Russell, F. In: Clarkson, B., Marks, P. A., Till, J. E. Eds. Differention of normal and neoplastic hematopoietic cells. Cold Spring Harbor. Cold Spring Harbor Press 1978;5:671–694.
Rey, M. A., Spire, B., Dormont, D. et al., Characterization of th RNA dependent DNA polymerase of a new human lymphotropic retrovirus (lymphaddenopathy associated virsu). Biochem. Biophys. Res. Comm. 1984; 121:126–133.
Heaton, K. W. Bile Salts in: Wright, R. Albertl., Kemm., Karrans, Millward-Sadzer, G H, Eds. Liver, Biliary Disease, London, W. B. Saunders, 1979:223–254.

*Primary Examiner*—Leonard Schenkman
*Attorney, Agent, or Firm*—Browdy & Neimark

[57] ABSTRACT

A method is provided for treating a viral infection in a subject by administering a surfactant and/or a steroid so as to produce a high concentration thereof in the systemic circulation. The method is particularly applicable to the treatment of HIV infections. The use of surfactants and/or steroids in the production of pharmaceutical compositions is described.

14 Claims, 1 Drawing Sheet

VIABLE CELL COUNT OF NON-HIV INFECTED AND HIV-INFECTED
CELLS TREATED OR NOT TREATED WITH 1 : 2000 BILE SALTS.

( •———• NON-HIV-INFECTED CEM; x———x HIV-INFECTED CEM;
o———o NON-HIV-INFECTED CEM TREATED WITH BILE SALTS;
o-------o HIV-INFECTED CEM TREATED WITH SALTS FOR 6h;
x-------x HIV-INFECTED CEM GROWN IN BILE SALTS FOR 7 DAYS.)

METHOD AND COMPOSITION FOR THE TREATMENT AND PREVENTION OF VIRAL INFECTIONS

This invention relates to a method and composition for the treatment and prevention of viral infections and particularly, but not exclusively to the treatment and prevention of infections of human immuno-deficiency virus (HIV) in human beings.

Acquired Immune Deficiency Syndrome (AIDS) has been described as "a modern plague: the first great pandemic of the second half of the twentieth century". The quest for an effective therapy for AIDS has become a major priority for research, but despite a massive commitment of resources, few drugs are available for therapy all have significant side effects and none is curative.

The causative agent of AIDS is a retrovirus previously referred to as HTLV-III or LAV, but now referred to as HIV. Current therapies proposed for combatting HIV infections generally involve the use of anti-viral agents which interfere with viral replication, for example by inhibiting reverse transcriptase. Such agents are generally highly cytotoxic and despite the limited success which has been achieved with such anti-viral agents as AZT (Zidovudine), no effective treatment of AIDS has been found to date. A proposal has been made (Reimund, E; 1986)[1] that butylated hydroxytoluene (BHT) may be of value in combination drug therapy of HIV. This is by analogy with a proposed treatment of Newcastle disease in chickens, where BHT is incorporated into feed.[2] However, the effect of BHT against HIV or any other retrovirus has not been investigated and there is no evidence that BHT could be used as an effective agent in combatting HIV infections.

It has now been surprisingly found that bile salts and related compounds both inhibit viral replication of HIV in an established line of human T4 cells and selectively destroy persistently HIV-infected cells at a concentration which is without apparent cytotoxic effect on non-infected cells, and this has led to the possibility of the therapeutic use of bile salts and related compounds systemically to combat virus infections.

Thus according to one aspect of the present invention there is provided a method of treating a viral infection in a subject, which comprises introducing a surfactant into the systemic circulation so as to create a plasma concentration of the surfactant sufficient to combat the infection, but insufficient to produce a life-threatening side-effect. By "surfactant" is meant any generally non-toxic water-soluble surface active agent capable of lowering the interfacial tension of aqueous media. Such surfactants generally possess detergent properties. Typical surfactant molelcules useful in carrying out the invention include a hydrophobic portion and one or more substituents which are hydrophilic in nature.

Preferably the surfactant is an ionic surfactant, especially an anionic surfactant such as one containing at least one carboxylate group (—COOH). Any carboxylate groups in the surfactant used in a method of the invention may be in the form of the free acid or in the form of a salt with a pharmaceutically acceptable cation.

Steroids having surfactant activity have been found to be particularly useful in carrying out the method of the invention.

In a variation of the method of the invention, a steroid having essentially no activity as an ionic surfactant may be used.

Thus according to a further aspect of the invention there is provided a method of treating a viral infection in a subject, which comprises introducing a steroid into the systemic circulation so as to create a plasma concentration of steroid sufficient to combat the infection, but insufficient to produce a life-threatening side-effect.

In accordance with a further aspect of the invention a surfactant and/or steroid may be used in the production of injectable pharmaceutical preparations in order to reduce the content of infectious virus, pro-virus or virus-infected cells therein. Such preparations include whole blood (for transfusion), blood plasma or other blood fractions or components. (e.g. Factor VIII).

Preferably any steroid used in carrying out the method of the invention should be essentially free of pronounced biological activity (other than the desired anti-viral activity) and in carrying out the method of the invention one would normally seek to avoid use of steroids having androgenic, oestrogenic or adrenergic activity or steroids which are haemolytic. Thus oestrone, oestradiol, progesterone, cortisone, androsterols and testosterol are less preferred, whereas fusidic acid (which has antibacterial activity) may be particularly useful. Other steroidal antibiotics which may be used include cephalosporin $P_1$ and helvolic acid. The precise chemical structure of the selected steroid is not unduly critical, but it will be appreciated that certain side-effects (for example androgenic side-effects) can be avoided by using steroids containing at least 22 and preferably at least 24 carbon atoms. It is also advantageous to utilise a steroid which is a normal human metabolite or one which has surfactant properties for example fusidic acid.

Useful steroids may be selected from those having the formula:

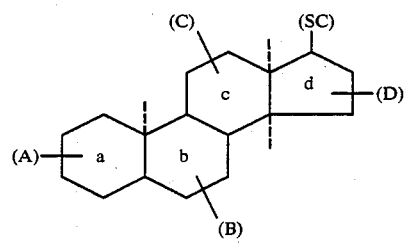

wherein
(SC) is an optionally branched aliphatic side chain, optionally substituted by —OH, =O, =NH, —NH$_2$, COOH, —COOR (wherein R represents $C_{1-6}$ alkyl, or a pharmacologically acceptable anion) or —COOX (wherein X is a residue of an amine or amino acid).

A, B, C and D each represent one or more optional substituents independently selected from HO, esterified hydroxy, =O, halogen, $C_{1-4}$ alkyl and epoxy, the dotted lines indicate optional angular methyl groups, and rings a, b, c and d are optionally unsaturated.

Any esterified hydroxy groups may be esterified with $C_{1-4}$ carboxy acids or phosphate groups.

Within this class, the so-called "bile salts" or "bile acids" have been found to be particularly effective in inhibiting HIV infections. In the literature, the terms "bile salts" and "bile acids" are used interchangeably. At physiological pH bile acids are ionised and are accompanied by plentiful cations, so it is strictly correct to refer to them as "bile salts".

Common mammalian bile acids are all C24 steroids of the 5 beta series with a carboxyl group at C24 and 1, 2 or 3 hydroxyl groups as nuclear substituents. Such bile acids (and their salts) are preferably used in the method of the invention, as well as related oxo-acids. Bile acids frequently occur as peptide conjugates with amino acids such as, for example, glycine and taurine. The use of conjugated bile salts is thus encompassed by the method of the invention. In general, bile acids may be conjugated with any amino acid of the formula $NH_2-X-A$ where A is an acidic moiety, for example a carboxy (—COOH) or sulpho (—$SO_3H$) group and X is an aliphatic. cycloaliphatic, heterocyclic or aromatic entity, preferably containing 1 to 10, most preferably 1 to 6 carbon atoms. Thus X may be the residue of any of the amino acids of normal metabolism. Examples of specific bile acids which may be used in accordance with the method of the invention include cholic acid, deoxycholic acid, chenodeoxycholic acid, ursodeoxycholic acid, trihydroxycoprostanic acid, taurocholic acid and glycocholic acid.

Naturally occuring bile acids (also known as "bile salts" see above) are naturally occuring components of bile and are synthesised from cholesterol in the liver. In normal healthy individuals bile produced by the liver and stored in the gall bladder passes via the common bile duct into the duodenum where it participates in the digestion of lipids. Most of the bile acids entering the duodenum are reabsorbed in the small intestine where they are returned to the liver via the portal vein. The circulation between the liver, common bile duct, duodenum, small intestine and portal vein is referred to as the "enterohepatic circulation" and in health, bile salts are present in the systemic circulation at very low concentration. In certain pathological conditions (including biliary obstruction and hepatic cirrhosis) elevated levels of bile salts may enter the systemic circulation. Levels up to 100 times normal are observed, but apart from occasionally producing such symptoms as pruritis, have no serious toxic side effects.[3] For a discussion of bile salts and their normal function reference is made to "Liver and Biliary Disease" ed. Wright et al. 1979, pp 233-254.[4]

In carrying out the methods of the invention, the desired surfactant and/or steroid may be introduced into the systemic circulation by any convenient means. Preferably the surfactant and/or steroid is introduced parenterally. Thus they may be administered by injection, intravenously intramuscularly sub-cutaneously. intrathecally or into a body cavity, e.g. intraperitoneally or intrapleurally. Other methods of administration may be adopted, for example rectal administration in the form of a suppository as an inhaled aerosol spray or oral administration, when the surfactant and/or steroid is preferably administered sub-lingually so as to enter the systemic circulation and by-pass the portal circulation.

The use of a surfactant and/or steroid in the manufacture of pharmaceutical compositions for use in treating viral infections (particularly infections with retroviruses, e.g. HIV) in the manner described above forms a further aspect of the present invention.

According to its more specific aspects, the invention further includes the use of a bile acid or derivative thereof in the manufacture of a pharmaceutical composition for use in the treatment of a viral infection in a subject, particularly in the treatment of subjects infected with HIV.

The use of bile acids in the treatment of viral infections has not been described hitherto, although oral adminstration of bile acids has been used for treating certain types of gallstones. However when bile acids are administered orally, they would not normally enter the systemic circulation since they would be absorbed in the small intestine and enter the enterohepatic circulation. Parenteral injection of radioactively labelled bile acids has been described[5], but for the purposes of experimental physiology only (to investigate the rate of breakdown of bile salts in the bloodstream). Parenteral administration of bile acids for therapeutic purposes has not been described hitherto.

The invention thus further provides pharmaceutical compositions for use in treating a viral infection in a subject comprising at least one bile acid or derivative thereof and a pharmaceutical acceptable excipient, said composition being adapted to administration by a route capable of producing an elevated concentration of bile acid in the systemic circulation, with the proviso that where the composition is in the form of a parenteral solution, the bile acid or derivative is not radioactively labelled. Preferred forms of pharmaceutical composition according to the invention comprise injectible solutions or suspensions, suppositories, aerosol sprays and dosage forms adapted for oral and particularly sub-lingual administration.

The compositions may comprise conventional pharmaceutically acceptable diluents or carriers. Thus typical injectible solutions will comprise sterile pyrogen-free media, e.g. normal saline and optionally include buffering agents, stabilising agents and preservatives. Suppositories will include excipients such as waxes and glycerol, while aerosol sprays will include, for example, an easily volatilised carrier such as, for example, ethanol.

In order to maintain an effective plasma concentration of surfactant and/or steroid in the systemic circulation (e.g. about 250 mg/l), it is preferable to administer at least 1.5 g per day, more preferably from 1.5 to 3.0 g per day of surfactant and/or steroid. Conveniently the surfactant and/or steroid is administered in divided doses. e.g. in doses of from 100 mg to 1 g up to three times per day. A particularly convenient dosage unit contains about 500 mg of surfactant and/or steroid.

Other examples of compositions according to the invention are topical compositions for protecting a subject against a viral infection. Such compositions may comprise a bile acid or derivative thereof and an excipient adapted for topical application. Such compositions may for example be in the form of creams, ointments, lotions, solutions or gels. Topical composition in forms suitable for vaginal use (e.g. creams, ointments, gels, foams and soluble pessaries) can offer protection against transmission of viral infections during sexual intercourse. These compositions may advantageously contain a spermicidally active agent.

The following example illustrates the anti-viral activity of bile acids.

EXAMPLE

1. VIRUSES AND CELL CULTURES

A human T-cell line (CEM) chronically infected with the CBL-1 strain of HIV was used in the experiments described below. Persistently infected and non-infected cells were grown in suspension cultures in 25 cm flasks. Tissue culture growth medium consisted of RPMI 1640 supplemented with 10% foetal calf serum (FCS).

A. Bile Acids

Bile acids in the form of bile salts containing a mixture of sodium cholate and sodium deoxycholate (Sigma) was made into a 1% stock solution in distilled water. Final dilution of the bile salts was carried out in RPMI 1640 prior to inoculation with cells (infected or non-infected).

B. Inactivation studies

Growth medium containing the appropriate amount of bile salts set up in 25 cm flasks (infected or non-infected) was added to the vessels making a final dilution of $5 \times 10^5$/ml.

Cells were exposed to growth medium containing bile salts under two experimental conditions: (a) 6 h, and (b) continuously for 7 days. In the case of (a), the cells after exposure were pelleted, washed in PBS and placed in fresh growth medium containing no bile salts. Additional growth medium (50%) was added to each culture after 3 days to maintain and promote cellular growth.

At days 3 and 7 evidence of viral activity was determined. Cultures were centrifuged and cell debris pelleted out. Cell debris was investigated by Western Blot, immunofluorescence and electron microscopy and re-cultured in fresh non-infected cells and re-examined over a further 7 days. Supernatant fluid was examined for reverse transcriptase and viral protein, ultracentrifuged for electron microscopy and re-cultured in fresh CEM non-infected cells for further confirmatory investigations over a further 7 days.

Similar investigations were carried out on control non-infected cells and infected cultures not exposed to bile salts.

2. DETECTION OF HIV

A. Enzyme Immunoassay for the Detection of Human Immunodeficiency Virus

Examination of culture fluids was made using the solid-phase sandwich-type enzyme immunoassay (Abbott Laboratories) in which human and rabbit polyclonal anti-HIV IgG are used as capture and probe antibodies respectively. Rabbit antibody was raised against the CBL-1 strain of HIV. Labelled goat-anti rabbit IgG was used to identify a positive reaction. Briefly, 200 µl of the sample was incubated overnight at room temperature with polystyrene beads coated with human anti-HIV IgG. After washing, rabbit antibodies are added and incubated for 4 hours at 40° C. with the goat-anti rabbit IgG labelled with horseradish peroxidase. Colour is added using o-phenylenediamine as substrate and absorbance is read at 492 nm using a Quantum 11 Dual Wavelength analyser, results being read as positive when the optical density is $>0.050$ plus the mean of 5 replicates of normal human plasma.

B. Western blots

After three and seven days incubation, cells were washed twice in cold phosphate-buffered saline (PBS). For direct lysis in Sodium Dodecyl Sulphate (SDS) the cells were dissolved in electrophoresis sample buffer (1% SDS, 0.1% mercaptoethanol, 2% glycerol, 0.01% bromophenol blue, 75 mM-Tris-HCL, pH 8.8) and heated for 2h to denature the proteins and inactivate any residual virus. After electrophoresis on SDS polyacrylamide gels by the method of Laemmli[6], proteins were transferred to nitrocellulose paper essentially as described by Towbin et al.[7], except that the transfer buffer was 3mM sodium carbonate, 10mM sodium bicarbonate, and 20% methanol[8] using a Transfor (Hoefer Scientific). The current was passed at 700mA over a 2h period. Molecular weights were estimated by comparison of electrophoretic mobilities with prestained protein molecular weight standards (Bethesda Research Laboratories).

Protein binding sites on the transfers were blocked before further analysis by soaking in PBS containing 0.05% Tween 20 for 1 h at room temperature with constant agitation.

C. Immunological detection of protein on nitrocellulose transfers

Transfers were incubated at room temperature with constant agitation in PBS containing 0.03% Tween 20 in which human antisera had been diluted (1:100). After 1 h the transfers were washed three times in PBS-Tween, incubated as above with PBS-Tween containing a 1:1000 horseradish peroxidase-conjugated anti-globulin (Miles Scientific Slough, UK). After 1 h and a similar washing cycle, antibody binding bands were revealed by incubation with aminoethylcarbazole.

D. Immunofluorescence

An indirect immunofluorescence test was performed. For this test cells were smeared on to glass slides, dried at room temperature for 1 h and fixed with acetone at room temperature for 10 minutes. Cell smears were treated with appropriate diluted anti-HIV human serum (1:50, or 1:100) in PBS at 37° C. for 30 minutes, washed with PBS and treated with fluorescein-conjugated rabbit anti-human IgG (δ-chains) (Miles Scientific) at 37° C. for 30 minutes. The smear was then covered with a cover glass and examined with a Nikon inverted microscope with HBO-100W Mercury lamp illuminator.

E. Electron microscopy

The cells were washed three time with PBS and the cell pellet was fixed in 2% glutaraldehyde in phosphate buffer, pH 7.2 at 4° C. for 60 minutes. The cells were washed twice with phosphate buffer, post-fixed in 1% OsO4 in barbital acetate buffer (pH 7.4) at 4° C. for 30 minutes dehydrated through a graded series of ethanols and then embedded in Epon 812. Ultrathin sections were made on a Cambridge-Huxley Ultra-microtome and mounted on carbon-evaporated grids. The sections were stained with uranyl acetate and then basic lead citrate and examined with an electron microscope (Philips).

F. Reverse Transcriptase Assay (RT)

Cell-free culture fluid (4ml) was assayed for RT activity as described by Gallo et al.[9]. HIV reverse transcriptase activity was measured in virus solubilizing buffer (0.8 mM/l, NaCl, 0.5% triton X 100, 0.5 mM/l phenylmethylsulfonyl fluoride, 20% glycerol, 50 mM/l Tris pH 7.9, 1 mM dithiothreitol). The polymerase reaction mixture (80 μl) contained 50 mmol/l Tris HCl pH 7.9, 20 mmol/HCl, 1 mmol/l dithiothreitol, 5 mmol/l MgCl$_2$, 10 μCi tritiated thymidine triphosphate (30 Ci/mmol), and 0.1 OD/ml of poly-A-oligo-dT $_{12-18}$ as template primer[10].

The above experiments were repeated using the U937 cell line with similar results.

DISCUSSION

It can be seen from the results depicted in FIG. 1 that CEM cells were tolerant to bile salts. Thus, although uninfected CEM cells did not replicate in tissue culture media containing bile salt concentrations of 1:100 and 1:1000 final dilution (5000 and 500 mg/l), a 1:2000 (250 mg/l) concentration of bile salts did markedly affect cellular replication or survival (FIG. 1). This level of bile salts did, however, inhibit the growth and survival of persistently HIV infected CEM cells which had either been exposed to bile salts over (1) a 6 h period, or (2) growth in the presence of bile salts over a 7 day period.

The results show that HIV is inactivated by bile salts. Thus, direct examination of HIV persistently infected cultures exposed to bile salts (6 h or 7 days) indicated no cellular replication and limited survival of original inoculum. Both total and viable cell numbers markedly declined in exposed infected cultures, as compared with non-infected and HIV infected cultures not exposed to bile salts (FIG. 1). No evidence of HIV replication was found in bile salt treated cultures after examination of cells or supernatant, as determined by electron microscopy, Western blot, immunofluorescence, reverse transcriptase or enzyme imunoassay.

Cellular material and supernatant from bile salt treated cultures recultured with non-infected CEM cells also indicated no viral activity when examined after 3 and 7 days.

A summary of the data is presented in Table 1 and represents data obtained from the original examination of cultures after 3 and 7 days post treatment. Similar results were obtained after a 6 h or 7 day continual exposure.

TABLE 1
SUMMARY OF OBSERVATIONS MADE ON HIV INFECTED AND NON-INFECTED CULTURES EXPOSED TO 1:2000 (250 mgs/l) OF BILE SALTS

| CULTURES | TYPE OF EXAMINATION | | | | | |
|---|---|---|---|---|---|---|
| | EM | WB | | IF | RT | EIA |
| | | P24 | p41 | | | |
| Non-infected CEM (−ve control) | − | − | − | − | − | − |
| Bile salt exposed HIV infected CEM Cells (Test) | − | − | − | − | − | − |
| HIV infected CEM (+ve control) | + | + | + | + | + | + |

The experiments confirmed that the persistently infected line of established T4 cells supported the production of large amounts of virus particles when harvested at the end of a 7-day growth cycle. Further it has been demonstrated that a 1/2000 concentration of bile salts (250 mg/l) does not inhibit the growth of uninfected cells over a similar period of time.

However, the addition of bile salts to cultures of HIV-infected cells surprisingly selectively destroys the persistently HIV-infected cells and eliminates all evidence of virus, as assessed by 5 separate methods. In addition both the centrifuged T cells and the supernatants failed to infect fresh cultures of cells confirming that no infectious virus remained. It appeared immaterial whether the infected cells were exposed to bile salts for 6 hours only, or continuously for 7 days, since in neither case was there evidence of virus. A particularly unexpected finding was that in both of these situations no viable cells remained either. This was in striking contrast to the healthy growth of uninfected cells in the presence of bile salts; and to the continual survival and growth of persistently infected cells, albeit with some evidence of viral lysis, when untreated with bile salts.

Further investigations on the effect of fusidic acid on HIV-infected CEM cells showed an inhibitory effect at concentrations from 10–200 μg/ml.

Although we do not wish to be limited by theory, it is postulated that the anti-viral activity of surfactants and steroids according to the invention stems from a disruption of the viral lipid envelope caused by these substances.

The following examples illustrate dosage forms suitable for use in carrying out the method of the invention.

A. Injectable Solution

| | |
|---|---|
| Cholic acid (Na salt) | 500 mg |
| Sodium hydrogen phosphate buffer to pH 7 | |
| Pyrogen free water | qv |

B. Injectable Solution

| | |
|---|---|
| Fusidic acid (Na salt) | 500 mg |
| Sodium hydrogen phosphate buffer to pH 7 | |
| Pyrogen free water | qv |

C. Injectable Solution

| | |
|---|---|
| Bile salts* | 400 mg |
| Sodium hydrogen phosphate buffer to pH 7 | |
| Pyrogen free water | qv |

*mixture of cholic acid, deoxycholic acid, chenodeoxycholic acid (Na salts)

D. Sublingual Tablet

| | |
|---|---|
| Bile salts | 500 mg |
| Glucose | 75 mg |
| Mg stearate | 2 mg |

E. Vaginal Pessary

| | |
|---|---|
| Fusidic acid | 500 g |
| Hard parafin wax | 500 g |
| PEG 1500 | 250 g |

REFERENCES

1. Reimund, E. Envelope perturbation and AIDS Lancet 1986; 2: 1159.
2. Brugh, M. Butylated hydroxytoluene protects chickens exposed to Newcastle disease virus. Science 1977; 197: 1291-92.

3. Neale, G., Lewis, B., Weaver, V., Panveliwalla, D. Serum bile acids in liver disease. Gut 1971; 12: 145-152.
4. Heaton, K. W. Bile salts. In: Wright, R., Alberti, K. G. M. M., Karran, S., Millward-Sadler, G. H., Eds. Liver and biliary disease. London: W. B. Saunders, 1979:233-254.
5. Cowen, A. E., Korman, M. G., Hofmann, A. F. Thomas, P. J. Plasma disappearance of radioactivity after intravenous injection of labelled bile acids in man. Gastroenterology 1975;68:1567-1573.
6. Laemmli, U. K. Cleavage of structural proteins during the assembly of the head of bacteriophage T4. Nature, London 1970;227:680-685.
7. Towbin, H., Staehelin, T. and Gordon, J. Electrophoretic transfer of proteins from polyacrylamide gels to nitrocellulose sheets: procedure and some applications. Proc. Nat. Acad. Sci., U.S. 1979; 76:4350-4354.
8. Dunn, S. D. Effects of modification of transfer buffer composition and the renaturation of proteins in gels on the recognition of proteins on Western blots by monoclonal antibodies. Analyt. Biochem. 1986; 157: 144-153.
9. Gallo, R. C., Gallagher, R. E. and Russell, F. In: Clarkson, B., Marks, P. A., Till, J. E. Eds. Differentiation of normal and neoplastic hematopoietic cells. Cold Spring Harbor. Cold Spring Harbor Press 1978;5:671-694.
10. Rey, M. A., Spire, B., Dormont, D. et al. Characterisation of the RNA dependent DNA polymerase of a new human lymphotropic retrovirus (lymphadenopathy associated virus). Biochem. Biophys. Res. Comm. 1984; 121: 126-133.

We claim:

1. A method for the treatment of patients infected with human immuno-deficiency virus (HIV) comprising administering an effective amount of a bile acid or derivative thereof.

2. A method in accordance with claim 11, wherein said bile acid is selected from the group consisting of cholic acid, deoxycholic acid, chenodeoxycholic acid, ursodeoxycholic acid, trihydroxycoprostanic acid, taurocholic acid and glycocholic acid.

3. A method in accordance with claim 1, wherein said bile acid or derivative thereof comprises a bile acid conjugated with an amino acid of the formula NH$_2$-X-A where A is an acidic moiety selected from COOH and SO$_3$H groups and X is an aliphatic, cycloaliphatic, heterocyclic or aromatic entity, containing 1 to 10 carbon atoms.

4. A method in accordance with claim 3, wherein X contains 1-6 carbon atoms.

5. A method in accordance with claim 1, wherein said bile salt or derivative thereof is administered into the systemic circulation.

6. A method in accordance with claim 5, wherein said bile salt or derivative thereof is administered in an amount which creates a plasma concentration sufficient to combat the infection but insufficient to produce a life-threatening side effect.

7. A method in accordance with claim 1, wherein the derivative is a salt, ester or amide.

8. A method in accordance with claim 6, wherein a plasma concentration of at least 50 mg/liter is maintained.

9. A method in accordance with claim 6, wherein a plasma concentration of at least 100 mg/liter is maintained.

10. A method in accordance with claim 6, wherein a plasma concentration of at least 200 mg/liter is maintained.

11. A method for preventing replication of human immuno-deficiency virus (HIV) in HIV infected cells comprising contacting the HIV-infected cells with an effective amount of a bile acid or derivative thereof.

12. A method in accordance with claim 11, wherein said effective amount is an amount effective to prevent substantial replication of the virus without markedly affecting the survival of non-infected cells.

13. A method in accordance with claim 11, wherein said bile acid is selected from the group consisting of cholic acid, deoxycholic acid, chenodeoxycholic acid, ursodeoxycholic acid, trihydroxycoprostanic acid, taurocholic acid and glycocholic acid.

14. A method in accordance with claim 11, wherein said bile acid or derivative thereof comprises a bile acid conjugated with an amino acid of the formula NH$_2$—X—A where A is an acidic moiety selected from COOH and SO$_3$H groups and X is an aliphatic, cycloaliphatic, heterocyclic or aromatic entity, containing 1 to 10 carbon atoms.

* * * * *